United States Patent [19]

Wasserman et al.

[11] 4,163,743
[45] Aug. 7, 1979

[54] BETA-LACTAMS, THEIR PRODUCTION FROM AZETIDINE CARBOXYLIC ACIDS, INTERMEDIATES THERETO AND DERIVATIVES THEREOF

[75] Inventors: Harry H. Wasserman; Alan W. Tremper, both of New Haven, Conn.

[73] Assignee: Research Corporation, New York, N.Y.

[21] Appl. No.: 831,441

[22] Filed: Sep. 8, 1977

[51] Int. Cl.$^2$ ............... C07D 205/08; C07D 407/06; C07D 403/06; C07D 405/06

[52] U.S. Cl. ............... 260/239 A; 260/326.13 B; 260/326.15; 260/338; 260/340.7; 260/340.9 R; 260/330.3

[58] Field of Search ............... 260/239 A, 326.5 FM, 260/340.7, 340.9 R, 338

[56] References Cited
PUBLICATIONS

R. T. Dean et al., J. Amer. Chem. Soc. 98, 7448–49 (1976).
Blaha et al., J. Het. Chem. 6, 216 (1966).

Primary Examiner—Mark L. Berch
Attorney, Agent, or Firm—Haight & Huard

[57] ABSTRACT

Azetidine-2-carboxylic acids are transformed readily to the corresponding beta-lactams by iminium salt formation and reaction of the salt with a suitable nucleophile. The beta-lactams and substitution products thereof are useful intermediates in the synthesis of biologically active lactams such as nocardicin.

9 Claims, No Drawings

BETA-LACTAMS, THEIR PRODUCTION FROM AZETIDINE CARBOXYLIC ACIDS, INTERMEDIATES THERETO AND DERIVATIVES THEREOF

CROSS-REFERENCE TO RELATED APPLICATION

A method for preparing azetidine carboxylic acids from gamma-lactone starting materials via low temperature dianion oxygenation is described in copending, commonly assigned U.S. Patent application Ser. No. 736,343 filed Oct. 28, 1976, the contents of which are incorporated by reference herein.

BACKGROUND OF THE INVENTION

This invention was supported in part by Grant GM-07874 from the National Institutes of Health.

This invention relates to a process for the conversion of azetidine carboxylic acids into corresponding beta-lactams, to intermediates useful in the synthesis of biologically active beta-lactams and to methods for the synthesis thereof.

Beta-lactams have received increasing study as an essential component in several families of compounds having useful biological, especially antibacterial, activity, e.g. the beta-lactam-thiazolidine ring (penam) system common to all penicillins and the beta-lactam-dihydrothiazine (cepham) nucleus common to the cephalosporins, and increasingly in monocyclic beta-lactams which have been recently described. For example, Hashimoto et al. in J.A.C.S. 98(10): 3023 (May 12, 1976), have described the structure of nocardicin, a monocyclic beta-lactam having antibacterial activity. A number of additional monocyclic beta-lactams, many of which are structurally similar to the bicyclic penicillins and cephalosporins, have been described in Belgium Pat. No. 830,934 and by Bose et al. in J.Med.Chem. 17(4): 541 (1974).

At present, most monocyclic beta-lactams are synthesized by the reaction devised by A. K. Bose wherein azidoacetyl chloride is reacted with a Schiff base to form the beta-lactam. While in general a satisfactory technique, the azidoacetyl chloride reagent is relatively expensive and dangerous to work with in large quantities due to the risk of explosions.

Accordingly, particularly in view of the increasing research being directed to the preparation of biologically active beta-lactams and the use of beta-lactam intermediates in the synthesis of valuable antibacterial compounds such as the penicillins, cephalosporins, nocardicins, etc., there is need for a safe and inexpensive method for the preparation of beta-lactams and related intermediates.

The aforementioned copending U.S. Patent application Ser. No. 736,343 describes a low temperature dianion oxygenation process first reported by Wasserman and Lipshutz in Tetrahedron Letters: 4613 (1976) for the preparation of beta-lactams from azetidine-2-carboxylic acid starting materials. The present invention provides an even more convenient, alternative procedure for accomplishing the same conversion, employing the reactivity of iminium salts toward nucleophiles, e.g. see R. T. Dean et al. in J.A.C.S. 98: 7448 (1976), the contents of which are incorporated by reference herein. The present invention is furthermore applicable to lactam formation in the presence of active (e.g. benzylic) hydrogen atoms in the substituent attached to the lactam ring nitrogen atom, which is not feasible in the previous low temperature dianion oxygenation process.

OBJECTS OF THE INVENTION

Accordingly, it is a general object of the present invention to provide a method for the nucleophilic substitution of azetidine carboxylic acids to directly form the corresponding beta-lactams, as well as iminium salt and perester intermediates useful in such a method.

Another object of the present invention is to provide a method for substituting the nitrogen atom of the lactam ring with a group bearing an active hydrogen atom thereon, e.g. in the beta position.

A further object of the present invention is to provide beta-lactam derivatives which are useful as intermediates in the synthesis of biologically active lactams.

An additional object of the present invention is to provide a method for the total synthesis of pharmaceutically useful monocyclic beta-lactams using inexpensive starting materials.

A more particular object of the present invention is to provide methods and intermediates for the synthesis of 3-aminonocardicinic acid and for the synthesis of nocardicins A and B therefrom.

Upon study of the specification and appended claims, further objects, features and advantages of this invention will become apparent to those skilled in the art.

SUMMARY OF THE INVENTION

Briefly, the above and other objects, features and advantages of the present invention are attained in one aspect thereof by providing a process for preparing a cyclic lactam which comprises subjecting an amino carboxylic acid of the general Formula I:

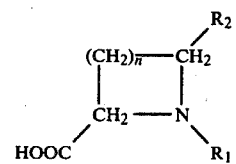

wherein
n is a positive integer of 1–10;
$R_2$ is hydrogen or alkyl of 1–6 carbon atoms; and
$R_1$ is aliphatic or cycloaliphatic of up to ten carbon atoms optionally interrupted by a sulfur or oxygen atom, or hydrocarbon aryl, alkaryl or aralkyl of 6–10 ring carbon atoms and 1–6 alkyl carbon atoms wherein $R_1$ is unsubstituted or substituted 1–3 times by at least one member selected from the group consisting of alkyl of 1–4 carbon atoms, alkoxy of 1–4 carbon atoms, —(CH$_2$)N—N—R'R" and —NR'R" wherein n has the above-indicated values and wherein R' and R" are each alkyl of 1–6 carbon atoms or collectively form a heterocyclic ring which is no more basic than imidazolyl and which contains 5–10 ring members and 1–3 nitrogen, oxygen or sulfur atoms, each of said members being unsubstituted or monosubstituted by alkyl of 1–4 carbon atoms or alkoxy of 1–4 carbon atoms;
or $R_1$ is a group of the formula $(CH_2)_n$—COOR$_1'$, an ester of the formula —CHR$_1$'COOR$_2$, an amide of the formula —CHR$_1$'CONR'R", an allylic group of the formula —CHR$_1$'CH=CHR$_2$ or a benzylic group of the formula —CHR$_1$'-phenyl-p-R$_2$ wherein n, $R_2$, R' and R" have the above-indicated values and $R_1'$ has the values given for $R_1$ to peracid reaction with an iminium salt oxidizing agent to form a corresponding cyclic lactam of the formula:

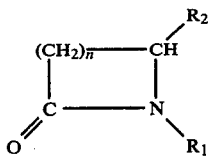

wherein $R_1$, $R_2$ and n have the above-indicated values.

In another aspect, the present invention provides novel N-substituted-2-azetidinium salts formed by decarbonylation of an azetidine carboxylic acid and a method for the oxidation thereof into the corresponding beta-lactam by nucleophilic addition of an organic oxidizing agent anion to the iminium salt.

In a further aspect, the present invention provides a method for the synthesis of biologically active beta-lactams, particularly compounds related to the penicillins, cephalosporins, nocardicins and the like, and intermediate beta-lactam products useful therein, particularly those containing an active hydrogen atom in the substitutent on the lactam nitrogen atom.

DETAILED DISCUSSION

In one aspect of the present invention, it has been found that alpha-carboxylic acid derivatives of cyclic amines having the general formula I

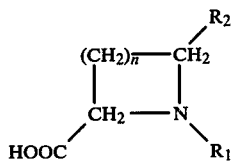

wherein $R_1$ and $R_2$ are as defined herein and n is a positive integer, preferably 1–10 and especially 1–3, can undergo decarbonylation to form an iminium salt which can then be reacted with a suitable nucleophilic oxidizing agent to form a corresponding lactam.

The starting materials of Formula I are readily available or can be prepared according to methods described in the aforementioned copending U.S. Patent application Ser. No. 736,343; the formation of iminium salts therefrom can be achieved analogously to the aforementioned method of R. T. Dean et al. The reaction sequence for this aspect of the present invention is set forth below:

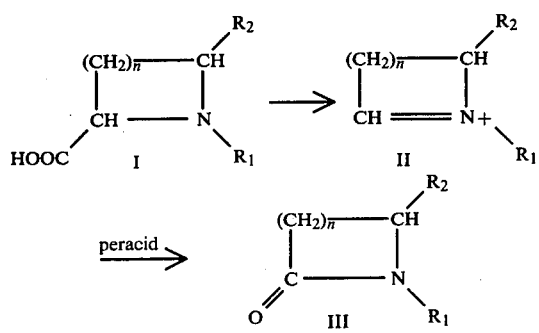

While not wishing to be bound by any theory of the invention, it is believed that conversion of the iminium salt II to the lactam III involves the formation of an intermediate perester IIA as an addition product of the peracid anion to the iminium salt which decomposes rapidly in the presence of a tertiary amine base to form the lactam in accordance with the following mechanism:

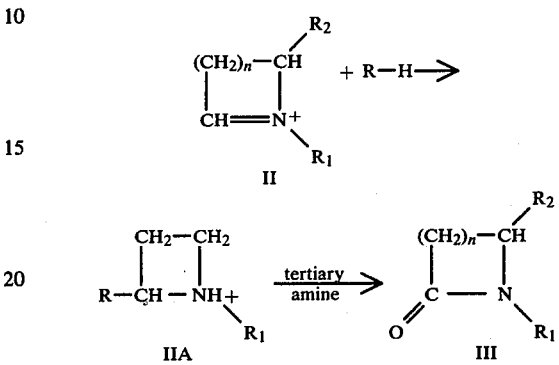

R in the above reaction scheme is the residue of any organic peracid or alkyl hydroperoxide meeting the criteria defined hereinafter.

$R_1$ in the above reaction scheme can be any organic radical having a carbon atom covalently bonded to the azetidine ring nitrogen atom which does not interfere with the decarbonylation and subsequent oxidation steps to form the desired beta-lactam product. $R_1$ values meeting the above criteria can be aliphatic, cycloaliphatic, hydrocarbon aromatic and hydrocarbon, heteroatomic or heterocyclic containing one or more nitrogen, oxygen and/or sulfur atoms as defined below.

Aliphatic or cycloaliphatic is preferably of up to six carbon atoms, e.g., alkyl, alkenyl, alkynyl, cycloalkyl or cycloalkenyl. Suitable alkyl groups include but are not limited to methyl, ethyl, n-propyl, isopropyl, n-butyl, isobutyl, sec.-butyl and tert.-butyl. Suitable alkenyl groups include but are not limited to vinyl, 2,2-dimethylvinyl, allyl, dimethylallyl, 1-propenyl, 1-butenyl, 2-butenyl, 3-meththyl-2-butenyl, 1-pentenyl and 2-pentenyl. Suitable alkynyl groups include but are not limited to propynyl, butynyl and pentynyl. Suitable cycloalkyl groups include but are not limited to cyclopropyl, cyclobutyl, cyclopentyl and cyclohexyl optionally substituted, e.g., by alkyl or alkenyl of up to four carbon atoms to form cycloalkylalkyl or cycloalkylalkenyl, e.g., cyclopropylmethyl. Suitable cycloalkenyl groups include but are not limited to cyclobutenyl, cyclopentenyl and cyclohexenyl optionally substituted, e.g., by alkyl or alkenyl of up to four carbon atoms to form cycloalkenylalkyl or cycloalkenylalkenyl, e.g., cyclobutenylethyl.

Hydrocarbon aromatic can be aryl, alkaryl, aralkyl, alkarylalkyl or aralkenyl wherein alkyl and alkenyl each have the above-indicated values. Hydrocarbon aryl is preferably phenyl, naphthyl or substituted phenyl; Hydrocarbon alkaryl is preferably alkylphenyl or substituted alkylphenyl, e.g., tolyl; hydrocarbon aralkyl is preferably phenylalkyl or substituted phenylalkyl of 1–4 carbon atoms in the alkyl substitutent, e.g., benzyl or phenylethyl; and hydrocarbon alkarylalkyl is preferably lower alkyl-phenyl-lower alkyl which can be unsubstituted or substituted as defined herein, e.g. methylbenzyl. Suitable substituents of the hydrocarbon aromatic group are 1-3 lower alkyl groups, e.g., methyl; 1-3 lower alkoxy groups, e.g., methoxy or ethoxy; and 1-3 halogen atoms, e.g., fluorine, chlorine or bromine. Suitable substituted hydrocarbon aromatic groups include but are not limited to o-, m- or p-tolyl, o-, m- or p-methoxyphenyl, o-, m- or p-fluorophenyl, o-, m- or p-chlorophenyl and alpha- or beta-naphthyl. Aralkenyl is preferably phenylalkenyl of 2-6 carbon atoms in the alkenyl substituent, e.g., phenylallyl.

$R_1$ can be a group of the formula $—(CH_2)_nR'R''$ or $NR'R''$ wherein n has the above-indicated values and $R'$ and $R''$ are each alkyl of 1-6 carbon atoms, aryl, aralkyl or alkaryl of 6-10 carbon atoms each of which is unsubstituted or substituted by 1-3 alkoxy of 1-4 carbon atoms or by a single heterocyclic ring of 4-7 members containing a total of 1-3 nitrogen, oxygen or sulfur hetero atoms; or $R'$ collectively form a heterocyclic ring which is no more basic than imidazolyl and which contains 5-10 ring members and 1-3 nitrogen, oxygen or sulfur atoms, each of said members being unsubstituted or monosubstituted by alkyl of 1-4 carbon atoms or alkolxy of 1-4 carbon atoms.

Monovalent heterocyclic ring substituents encompassed by the present invention are generally of 5-10, preferably 5 or 6 ring atoms of which 1-4, generally 1-3 and preferably 1 or 2, are oxygen, nitrogen and/or sulfur heteroatoms. The heterocyclic ring can be nonhydrogenated, e.g., imidazolyl, thiazolyl, etc.; partially hydrogenated, e.g., imidazolinyl, oxazolinyl, thiazolinyl, etc.; or completely hydrogenated, e.g., piperazinyl, morpholino, tetrahydropyrimidinyl, etc.

Suitable heterocyclic groups can be those derived from a five member heterocyclic ring containing a single heteroatom, e.g., furyl, thienyl or pyrrolyl; a five member heterocyclic ring containing two heteroatoms, e.g., pyrazolyl, imidazolyl, oxazolyl, oxazolinyl, isoxazolyl, isoxazolinyl, thiazolyl or thiazolinyl; a five member heterocyclic ring containing three heteroatoms, e.g., triazolyl, oxadiazolyl, thiadiazolyl, dioxazolyl and oxathiazolyl; or a five member heterocyclic ring containing four heteroatoms, e.g., tetrazolyl, oxatriazolyl and thiatriazolyl. Preferred heterocyclic groups derived from a five member heterocyclic ring are furyl, thienyl, pyrrolyl, pyrazolyl, imidazolyl, isoxazolyl and thiazolyl, especially thienyl.

Suitable heterocyclic groups can also be those derived from a six member heterocyclic ring containing a single heteroatom, e.g., pyridyl, pyranyl and thiopyranyl, preferably pyridyl; a six member heterocyclic ring containing two ring heteroatoms, e.g., dioxinyl, pyridazinyl, pyrimidinyl, pyrazinyl, piperazinyl, oxazinyl and morpholino, preferably pyridazinyl, pyrimidinyl, piperazinyl or morpholino; or a six member heterocyclic ring containing three ring heteroatoms, e.g., triazinyl, oxathiazinyl and oxadiazinyl. Preferred heterocyclic groups derived from a six member heterocyclic ring are pyridyl, pyridazinyl, pyrimidinyl, piperazinyl and morpholino.

Suitable heterocyclic groups can furthermore be those derived from a fused heterocyclic ring containing one six-membered ring fused to a five-membered ring wherein the six-membered ring is preferably hydrocarbon but can be interrupted by a single oxygen or nitrogen atom and wherein the five-membered ring contains one or two, preferably one, oxygen, nitrogen or sulfur heteroatoms, e.g., indolyl.

Presently preferred heterocyclic ring values for $R_1$ are furyl, thienyl, pyrrolyl, oxazolyl, imidazolyl and indolyl.

$R_1$ can furthermore be a group of the formula $—(CH_2)_n—R'''$ wherein n has the above-indicated values and $R'''$ is a group, preferably of general Formula V:

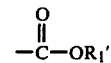

wherein $R_1'$ has the above-indicated values for $R_1$.

$R_2$ in the above formulae is preferably hydrogen but can also be lower alkyl of 1-6, preferably 1-3, carbon atoms, e.g. methyl, ethyl, n-propyl or isopropyl.

Where substitution is indicated for any radical on compounds in accordance with the present invention, the degree of substitution unless otherwise indicated is generally 1-3, preferably 1 or 2, and it will be appreciated that potentially limiting factors such as steric hindrance and the like will be taken into account by those skilled in the art to which this invention pertains. So that the activity and characteristic structure of the compounds of Formula II is predominantly that of an iminium salt, the sum of the molecular weights of the substituents thereon is generally less than about 300, preferably less than about 200, and these substituents generally contain a total of not more than 15, preferably not more than ten carbon atoms and generally not more than five, preferably not more than three, heteroatoms. The compounds can optionally be of the general Formula IV:

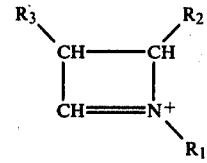

wherein $R_1$ and $R_2$ have the above-indicated values and $R_3$ is preferably hydrogen but can also be any of the values defined herein for $R_2$; these values can be introduced during formation of the azetidine carboxylic acid starting material of Formula I, e.g. in accordance with the methods of said copending U.S. Patent application.

Details for preparing compounds of Formula I wherein $R_1$ has the above-indicated values can likewise be found in the aforementioned copending U.S. Patent application. A limitation in the process described therein is that the $R_1$ substituent cannot contain an active hydrogen atom on the carbon atom which is covalently bonded to the lactam ring nitrogen atom, since this would be abstracted by the subsequent treatment with a strong base. As the reaction mechanism of the present invention is quite different and does not rely upon subsequent treatment with a strong base, this prior limitation is inapplicable so that $R_1$ can now include compounds which contain such an active hydrogen atom, e.g. allyl or benzyl groups or hydrogens alpha to an acid ester or amide; such compounds are prepared analogously to those compounds of Formula I described in said copending application.

The $R_1$ groups which may now be incorporated into the lactam ring accordingly can now include those containing active hydrogens on the carbon atom which is covalently bonded to the lactam ring nitrogen atom, such as alpha- to carboxyl or amide carbonyls, e.g.

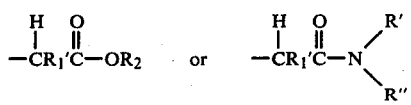

or allylic or benzylic hydrogens, e.g.

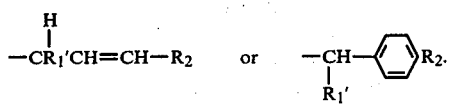

All of these active hydrogen atoms would have been removed in the earlier dianion oxygenation process but are not so subject to removal in accordance with the process of the present invention.

The azetidine carboxylic acid starting materials of Formula I can be converted into the corresponding iminium salts of Formula II by techniques well known to those skilled in the art which include but are not limited to (a) oxidation of a tertiary amine; (b) condensation of a carbonyl component with a secondary amine; (c) additions to amides; and (d) deacylation of alpha-tertiary amino acid acyl derivatives. Because of the high yields and regiospecificity obtainable in the last process, described by Dean et al. in the previously mentioned article, this method is presently preferred.

The corresponding aminocarboxylic acid of Formula I is reacted, e.g. at 0 degrees C., with a decarbonylating agent sufficiently strong to deacylate the carboxyl group and the reaction mixture gently warmed, e.g. to 35-45 degrees C., to drive off the carbon monoxide byproduct. The decarbonylation agents are generally toxic and appropriate known precautions must be used. Suitable such agents are well known in the art and include but are not limited to oxalyl chloride, phosphorus pentachloride, phosphorus trichloride, phosphorus oxychloride, thionyl chloride, trifluoroacetic acid, polyphosphoric acid, dimethylformamide-sulfur trioxide complex, etc. Of these, oxalyl chloride is presently preferred. Reaction temperatures and pressures are likewise conventional and can range from −70 degrees C. to room temperature or higher at atmospheric pressure, preferably at −20 to 25 degrees C. Heating the reaction mixture, e.g., to 80-100 degrees C. for about 1-10 minutes, generally facilitates the reaction.

The counterion portion of the azetidinium salts according to Formula II will vary depending on the particular reactants employed in the formation thereof but in general can be any acid anion characterized by being capable of forming salts with tertiary amines. Suitable such organic and inorganic acids are well known in the art and include but are not limted to alphatic, alicyclic, arylaliphatic, aromatic and heterocyclic mono- or polybasic carboxylic or sulfonic acids, e.g., formic acid, pivalic acid, oxalic acid, trifluoroacetic acid, methanesulfonic acid, ethanedisulfonic acid, beta-hydroxyethanesulfonic acid, p-toluenesulfonic acid, naphthalenemono- and -di sulfonic acids; and inorganic mineral acids, e.g., sulfuric acid, nitric acid, hydrochloric acid, hydrobromic acid, phosphoric acids such as orthophosphoric acid, etc.

The azetidinium salts of Formula II are not usually isolated but qualitatively confirmed, e.g. by the use of nuclear magnetic resonance or infrared spectroscopy. These iminium salts can, if desired, be isolated by simple removal of volatile materials in vacuo.

The formation of the beta-lactam via nucleophilic substitution of the azetidinium salt is effected by treatment with an oxidizing agent which is sufficiently strong to fully oxidize the iminium anion and add an oxygen atom thereto to form a carbonyl group at the unsaturated carbon atom in the azetidinium ring. The main criticality with respect to the oxidizing agent is that it be one with an oxidation potential which is sufficiently strong to oxidize the iminium salt yet sufficiently weak so as not to further oxidize the desired beta-lactam product. In addition, the oxidizing agent must be capable of nucleophilic addition to the iminium salt. Preferably, the oxidizing agent employed will be chosen to possess solubility properties consistent with those of the iminium salt being oxidized in order to ensure a rapid reaction rate in a non-aqueous reaction medium. Suitable such oxidizing agents are well known in the art and include but are not limited to the presently preferred peracids.

Peracid reaction with the iminium salt can conveniently be effected without separation by pouring a solution of the iminium salt into a cold, aprotic solvent and adding the peracid thereto dropwise. A wide variety or oxidizing agents can be employed in this step, which are well known in the art and include but are not limited to substituted aryl peracids, e.g. perbenzoic acid, m-chloroperbenzoic acid, p-chloroperbenzoic acid and methylperbenzoic acid; alkyl peracids, e.g. peracetic acid or per-trifluoroacetic acid; and alkyl hydroperoxides, e.g. t-butyl hydroperoxide.

Peracid addition is preferably acomplished in an inert diluent, i.e., one which does not deleteriously interfere with the desired reaction under the particular reaction conditions selected. Suitable inert diluents are well known in the art and are generally halogenated hydrocarbons. Suitable such diluents include but are not limited to methylene chloride, chloroform, carbon tetrachloride, 1,2-dichloroethylene, trichloroethylene, tetrachloroethylene, chlorobenzene, o-dichlorobenzene, trichlorobenzene (mixtures of isomers), bromobenzene, fluorobenzene, 1,2-dichloroethane, etc. These diluents can be used individually or as mixtures of two or more inert diluents which are miscible with each other in the particular ratio employed.

The perester intermediate of Formula IIA decomposes rapidly upon treatment with a strong base, e.g. a tertiary amine, to form the lactam of Formula III. In principle, any base whose corresponding acid has a dissociation constant comparable to that of presently preferred pyridine, preferably a $pK_b$ of at least $10^{-5}$, especially of at least $10^{-3}$, can be used. Suitable such bases are well known in the art and include but are not limited to monoalkylamines, e.g., methylamine, ethylamine, n-propylamine, isopropylamine, n-butylamine and isobutylamine; dialkylamines, e.g., dimethylamine, methylethylamine, diethylamine, di-n-propylamine, di-isopropylamine, di-n-butylamine and diisobutylamine; aryl- and aralkylamines, e.g., aniline and benzylamine; hydroxyalkylamines, e.g., ethanolamine and diethanolamine; cyclic amines, e.g., pyridine, pyrrolidine, piperidine, morpholine, thiomorpholine, piperazine and N-alkylpiperazines, e.g. N-methyl- or N-ethylpiperazine; and N-hydroxyalkylpiperazines, e.g., N-2-hydroxyethylpiperazine. Other suitable organic bases are quinoline, lutidine and 2,3,6-collidine. The inorganic salt of a peracid such as sodium m-chloroperbenzoate can be used in lieu of one mole of the organic base.

The beta-lactam product can then be isolated and purified by conventional techniques, which will be chosen depending on the particular molecular structure and state of matter obtained. Solids or liquids can both be chromatographed on florisil or alumina, e.g., using chloroform-ether as an eluent; liquids can be kugelrohr distilled under high vacuum.

It will be appreciated that the process of the present invention provides a simple manner for preparing beta-lactams bearing a wide variety of substituents on the lactam nitrogen atom. In this connection, $R_1$ is preferably straight-chain or branched alkyl, e.g., methyl, ethyl, n-propyl, isopropyl, n-butyl, isobutyl, sec.-butyl, tert.-butyl, n-pentyl, isopentyl, n-hexyl, n-heptyl, n-octyl, 2-ethylhexyl, n-nonyl, n-decyl, n-undecyl, n-dodecyl, n-tridecyl or n-tetradecyl; alkenyl, e.g., allyl or crotyl; alkynyl, e.g., propargyl; alkoxyalkyl, e.g., 2-methoxyethyl or 2-ethoxyethyl; the above corresponding groups having an oxygen or sulfur atom in the chain; tertiary aminoalkyl, e.g., wherein the amino groups is separated by at least two carbon atoms from the primary amine group, including N,N-dialkylaminoalkyl; cycloalkyl and cycloalkyl-alkyl primary amines, e.g. containing 3–8 ring carbon atoms, preferably 5 or 6, e.g., cyclopentyl, cyclohexyl, 2-cyclohexylethyl or 3-cyclohexylpropyl; azacycloalkyl, azacycloalkylalkyl and related cyclic groups, preferably containing a total of 5 or 6 ring members, with 1–2 of N and 0–1 of O or S as ring members in addition to ring carbon atoms and wherein the ring is at least one carbon removed from the amino group, e.g., by lower alkylene. Hydroxyl groups may lead to deleterious side reactions such as dehydration and polymerization and accordingly should be avoided.

Especially preferred as intermediates for subsequent synthesis of beta-lactam-containing compounds having pharmaceutical utility are those wherein the lactam nitrogen is substituted with an alkylene dialkoxy group of any desired chain length, preferably lower alkylene di-lower alkoxy of 1–8 carbon atoms in the alkyl group and 1–4 carbon atoms in each alkoxy group, e.g., ethylenedimethoxy. An additional preferred class of beta-lactams obtainable in accordance with the present invention is that wherein the lactam nitrogen is substituted by an alkenyl group of any desired chain length, preferably of 3–10 carbon atoms, in which the ethylenic unsaturation is spaced by at least one carbon atom from the lactam nitrogen, e.g., allyl. As with the acid-labile acetals, these alkenyl-substituted beta-lactams have latent functionality and facilitate expansion of the side chains to form a variety of end products. While an acidic enviornment is used in accordance with the process of the present invention, the reaction periods employed are sufficiently brief and the temperatures sufficiently low so as not to cause cleavage of ether groups when present.

Suitable alkenyl-substituted beta-lactams are formed from azetinium salt compounds in which $R_1$ is of the general Formula VI:

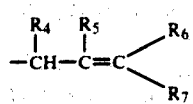   VI wherein $R_4$ has the above-indicated values for $R_1$, especially as in nocardicin; and $R_5$, $R_6$ and $R_7$ are each hydrogen or alkyl of 1–10, preferably 1–3, carbon atoms.

Suitable acetals are formed from azetinium salt compounds in which $R_1$ is of the general Formula VII:

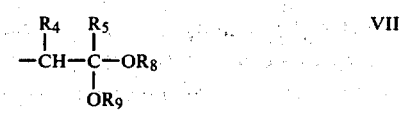   VII wherein $R_4$ and $R_5$ have the above-indicated values and $R_8$ and $R_9$ are each alkyl of 1–6 carbon atoms or $R_8$ and $R_9$, together with the oxygen atoms to which they are bonded, collectively form alkylenedioxy of 2–8 carbon atoms. Alkylenedioxy is preferably of 2–4 carbon atoms, e.g., ethylenedioxy, propylenedioxy, etc.

Substitution of the beta-lactam at the 3-position is readily accomplished according to techniques well known in the literature, e.g., see Kuhlein and Jensen, Liebigs Ann.Chem. 1974, pp. 369–402. As with the details of the iminium salt reactions, this can be achieved with a variety of reaction conditions. Preferred substituents at the 4-position of the lactam ring can be produced during ring formation; presently preferred are those substituents occurring at this position in the known active monocyclic beta-lactams, e.g., p-methoxyphenyl, o-nitrophenyl, o-aminophenyl, 1-(aminobenzyl)phenyl, 2-furanyl, p-carboxyphenyl and the like. Similarly, preferred substituents on the lactam nitrogen are those commonly occurring in antibacterially active monocyclic beta-lactams, e.g. p-acetylphenyl, diphenylmethylene, phenyl, p-methoxyphenyl, p-carboxyphenyl, p-carboxymethylphenyl and benzyl. An especially preferred substituent at the 3-position is the azide group $N_3$ because this group is readily reduced to the amino group $NH_2$, which in turn can be converted into a corresponding amide by suitable reaction with acid residues found in the penicillins and cephalosporins, e.g., phenylacetyl, phenoxyacetyl, 2-pentenoyl, n-pentanoyl, n-heptanoyl, p-hydroxyphenylacetyl, allythioacetyl, etc.

Compounds of this invention which contain a center of asymmetry are ordinarily obtained in the racemic form. The racemates can be separated into their optical antipodes in accordance with a plurality of known methods described in the literature; chemical separation is preferred. According to this procedure, diastereomers are formed from the racemic mixture by reaction with an optically active auxiliary agent. Thus, an optically active base can be reacted with the carboxyl group, or an optically active acid with the amino group, of a suitable compound of this invention. For example, diastereomeric salts of compounds containing a free carboxyl group can be formed with optically active amines, e.g., quinine, cinchonidine, brucine, hydroxyhydrindiamine, morphine, 1-phenylethylamine, 1-naphthylethylamine, phenyloxynaphthylmethylamine, quinidine and strychnine or basic amino acids, e.g, lysine, arginine and amino acid esters; or diastereomeric salts of basic compounds can be formed with optically active acids, e.g., (+)- and (−)-tartaric acid, dibenzoyl-(+)- and -(−)-tartaric acid, diacetyl-(+)- and -(−)-tartaric acid, camphoric acid, beta-camphorsulfonic acid, (+)- and (−)-mandelic acid, (+)- and (−)-malic acid, (+)- and (−)-2-phenylbutyric acid, (+)- and (−)-dinitrodiphenic acid or (+)- and (−)-lactic acid. In a similar manner, ester distereomers can be produced by the esterification of compounds containing a free carboxyl group with optically active alcohols, e.g., borneol, menthol or 2-octanol. The thus-obtained mixtures of diastereomeric salts and/or esters can be separated, e.g. by selective crystallization, and the desired optically active compounds can be produced by hydrolytic separation of the isolated diastereomeric compound.

A presently preferred aspect of the present invention relates to the synthesis of 3-aminonocardicinic acid (3-ANA), a useful intermediate in the synthesis of nocardicin. 3-ANA can be obtained using the method of the present invention in the following reaction sequence:

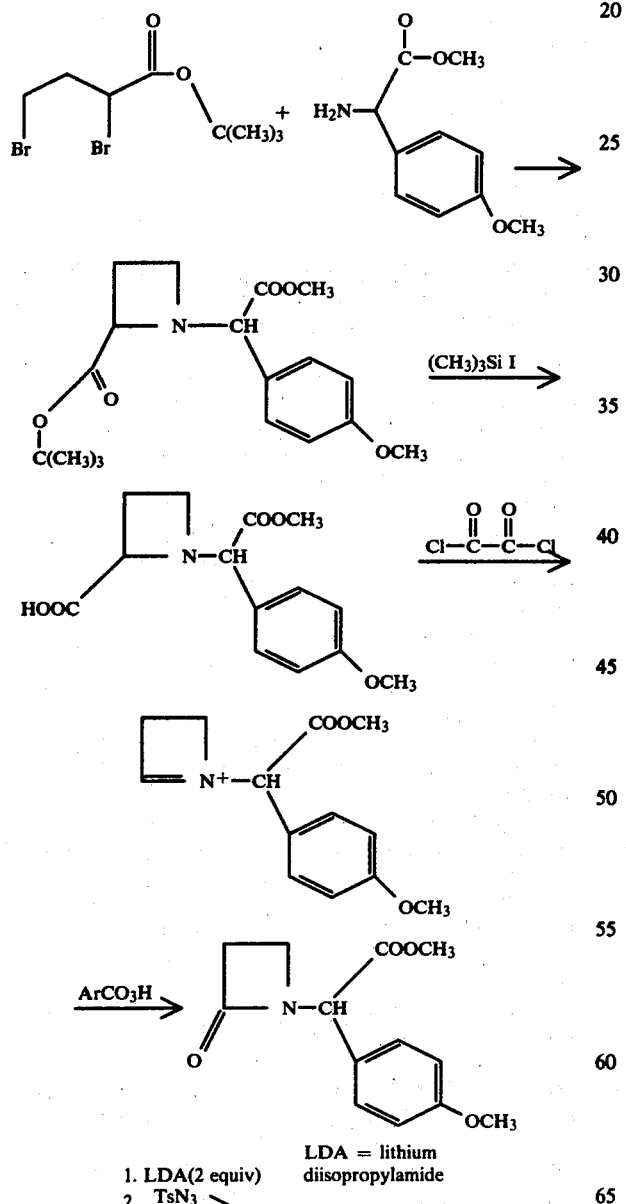

LDA = lithium diisopropylamide
TsN₃ = Tosylazide
Ar = phenyl or substituted phenyl

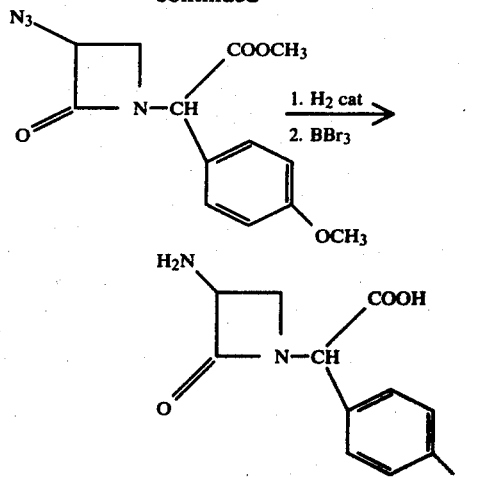

Especially preferred compounds of the present invention are those of the above formulae in which one or more of the substituents thereon have the following preferred values:

(a) $R_1$ is alkyl or alkenyl of up to six carbon atoms which is unsubstituted or substituted as aforesaid and which is optionally interrupted by a sulfur atom;

(b) $R_1$ is alkyl, hydrocarbon aryl, alkaryl or aralkyl monosubstituted by -NR'R'';

(c) $R_1$ is alkenyl of the formula

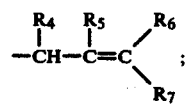

(d) $R_1$ is alkenyl of the formula

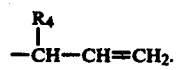

especially wherein $R_4$ is p-alkoxyphenyl or p-benzyloxyphenyl;

(e) $R_1$ is an acetal group of the formula

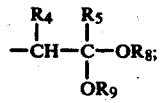

(f) $R_1$ is as in (e), wherein $R_4$ is p-alkoxyphenyl or p-benzyloxyphenyl;

(g) $R_2$ is hydrogen or alkyl of 1-3 carbon atoms, preferably hydrogen and especially as in (a) thru (f) inclusive;

(h) $R_3$ is alkyl of 1-4 carbon atoms, benzyl or benzhydryl, especially as in (a) thru (g) inclusive;

(i) $R_4$ is alkoxy, aryloxy, alkoxyaryl, aryloxyalkyl or aryloxyaryl, especially as in (g);

(j) $R_4$ is p-alkoxyphenyl or p-benzyloxyphenyl, especially as in (g)

(k) $R_5$ is hydrogen or alkyl of 1-3 carbon atoms, preferably hydrogen, especially as in (c) thru (j) inclusive;

(l) R$_6$ and R$_7$ are each hydrogen or alkyl of 1-3 carbon atoms, preferably hydrogen, especially as in (g) thru (k) inclusive;

(m) R$_8$ and R$_9$ are each alkyl of 1-3 carbon atoms, especially methyl or ethyl, or R$_8$ or R$_9$, together with the oxygen atoms to which they are bonded, form alkylenedioxy of 2-3 carbon atoms, especially as in (f) and (g) through (k) inclusive (n) azetinium salts of the partial formula

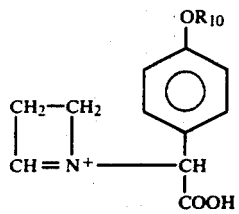

wherein R$_{10}$ is a cleavable hydroxyl masking group, preferably alkyl, alkanoyl, aroyl, arylalkyl, alkylsulfonyl, arylsulfonyl or trialkylsilyl and especially alkyl of 1-4 carbon atoms, e.g. methyl, or benzyl or benzhydryl;

(o) azetinium salts of the partial formula

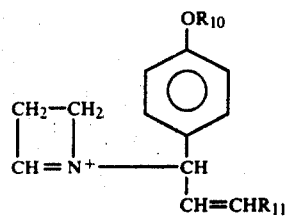

wherein R$_{10}$ is as defined in (n) and R$_{11}$ is hydrogen or alkyl of 1-6 carbon atoms, especially hydrogen;

(p) R$_1$ contains a heterocyclic ring as defined herein which is separated from the nitrogen atom to which R$_1$ is bonded by at least one carbon atom, e.g., by alkylene of 1-10, preferably 1-6, carbon atoms such as methylene, ethylene, n-propylene, etc., especially methylene and most especially as in (g) thru (m) inclusive;

(q) R$_1$ contains an hydrocarbon aryl, alkaryl or aralkyl ring as defined herein which is separated from the nitrogen atom to which R$_1$ is bonded by at least one carbon atom, e.g., by alkylene of 1-10, preferably 1-6, carbon atoms such as methylene, ethylene, n-propylene, etc., especially methylene and most especially as in (g) thru (m) inclusive. Particularly preferred such values for R$_1$ are benzyl or benzhydryl, either unsubstituted or substitued as defined herein; and (r) R$_1$ is an ester or dialkylamide of the formula

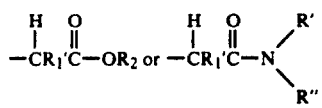

wherein R$_1$', R$_2$, and R" have the above-indicated values, especially as in (g) thru (m) inclusive.

Specific compounds of the present invention, in addition to those shown above and in the following examples, include but are not limited to the following counterions:

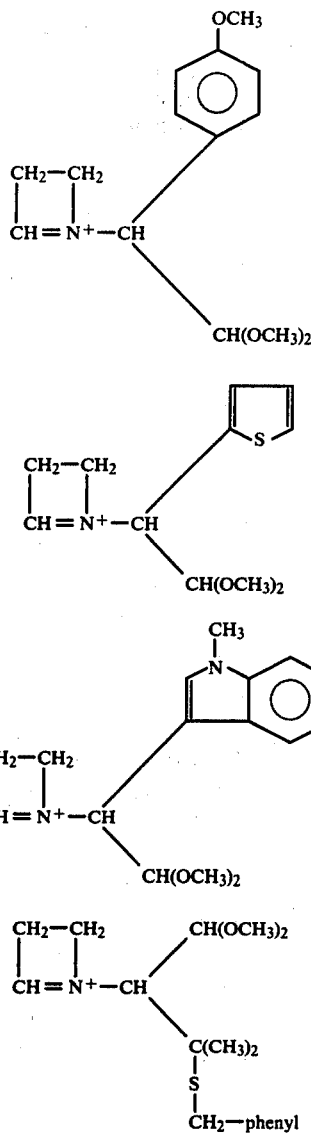

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. All temperatures are set forth uncorrected in degrees Celsius; unless otherwise indicated, all pressures are ambient and all parts and percentages are by weight. The values obtained by elemental analysis are within the usual limits of experimental error; all new products gave the expected parent peaks in the mass spectra and the expected absorption peaks in NMR and IR.

EXAMPLE 1

N-benzyl-2-azetidine carboxylic acid (2 mmol) was added slowly to excess oxalyl chloride at 0 degrees followed by gradual warming to 45 degrees (10 min.). The clear solution was then poured into cold, anhydrous ether, acidified with 10 drops of 70% perchloric acid and filtered to give N-benzyl-2-azetidinium perchlorate (95%). A suspension of this iminium salt in 10 ml of methylene chloride at 0 degrees was treated with 1 equivalent of 100% m-chloroperbenzoic acid followed by 2 equivalents of pyridine. The resulting reaction mixture was stirred for 40 min. and then poured into water. The organic layer was separated, washed with 5% NaHCO$_3$ and dried over Na$_2$SO$_4$. Evaporation of the solvent under reduced pressure afforded N-benzyl-2-azetidinone as the sole product (70%).

EXAMPLE 2

Following the procedure of Example 1 but using N-isobutyl-2-azetidine carboxylic acid, the product N-isobutyl-2-azetidinone was obtained in a yield of 70%.

EXAMPLE 3

Following the procedure of Example 1 but using N-2(p-methoxyphenyl)ethyl-2-azetidine carboxylic acid, the product N-2(p-methoxyphenyl)ethyl-2-azetidinone was obtained in a yield of about 75%.

EXAMPLE 4

Following the procedure of Example 1 but using N-cyclohexyl-2-azetidine carboxylic acid, the product N-cyclohexyl-2-azetidinone was obtained in a yield of 75%.

EXAMPLE 5

Following the procedure of Example 1 but using N-phenethyl-2-azetidine carboxylic acid, the product N-phenethyl-2-azetidinone was obtained in a yield of 78%.

The preceding examples can be repeated with similar success by substituting the generically or specifically described reactants and/or operating conditions of this invention for those specifically used in the examples. From the foregoing description, one skilled in the art to which this invention pertains can easily ascertain the essential characteristics thereof and, without departing from the spirit and scope of the present invention, can make various changes and modifications to adapt it to various usages and conditions.

What is claimed is:

1. A process for preparing a lactam which comprises reacting an ammonium salt, the anionic portion of which is the anion of an acid which is capable of forming iminium salts by oxidative decarboxylation of a corresponding tertiary amine and the cationic portion of which is a cation of the formula

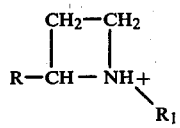

wherein
R is the residue of a hydrocarbon aryl peracid, alkyl peracid or alkyl hydroperoxide formed by removal of a single hydrogen atom therefrom; and
R$_1$ is selected from the group consisting of:
(a) an alkenyl group of the formula

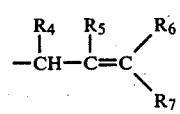

wherein R$_4$ is p-alkoxyphenyl or p-benzyloxyphenyl and R$_5$, R$_6$ and R$_7$ are each hydrogen or alkyl of 1–3 carbon atoms; and
(b) an acetal of the formula

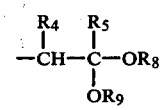

wherein R$_4$ and R$_5$ have the above-indicated values while R$_8$ and R$_9$ are each alkyl of 1–6 carbon atoms or together form alkylenedioxy of 2–4 carbon atoms;
with a strong base having a pK$_b$ of at least $10^{-5}$ to form a corresponding cyclic lactam of the formula:

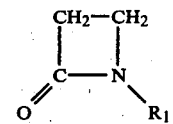

wherein R$_1$ has the above-indicated values.

2. A process according to claim 1, wherein R is the residue of a compound selected from the group consisting of perbenzoic acid, m-chloroperbenzoic acid, p-chloroperbenzoic acid, methylperbenzoic acid, peracetic acid, pertrifluoroacetic acid and t-butylhydroperoxide.

3. A process according to claim 2, wherein R$_1$ is as defined in (a).

4. A process according to claim 3, wherein R$_5$, R$_6$ and R$_7$ are each hydrogen.

5. A process according to claim 3, wherein R$_4$ is p-benzyloxyphenyl.

6. A process according to claim 2, wherein R$_1$ is as defined in (b).

7. A process according to claim 6, wherein R$_4$ is p-benzyloxyphenyl.

8. A method for synthesizing 3-amino-nocardicinic acid, which comprises:
(a) reacting an ammonium salt, the anionic portion of which is the anion of an acid which is capable of forming iminium salts by oxidative decarboxylation of a corresponding tertiary amine and the cationic portion of which is a cation of the formula

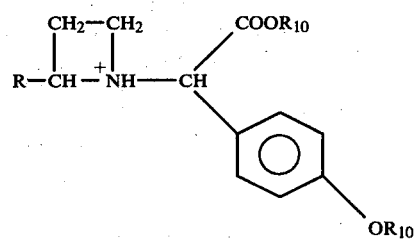

wherein
R is the residue of a hydrocarbon aryl peracid, alkyl peracid or alkyl hydroperoxide formed by removal of a single hydrogen atom therefrom; and
R$_{10}$ is alkyl of 1–4 carbon atoms, benzyl or benzhydryl
with a strong base having a pK$_b$ of at least $10^{-5}$ to form a corresponding beta-lactam of the formula:

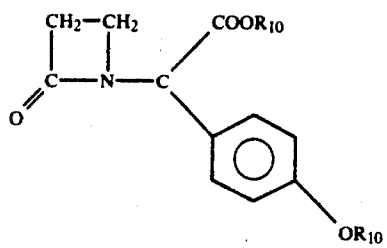
(b) introducing an azide group -$N_3$ into the 3-position of said beta-lactam to form a corresponding beta-lactam azide of the formula
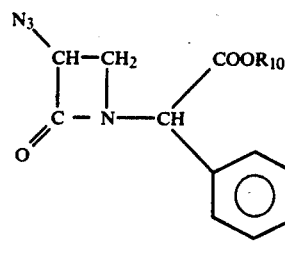
and
(c) reducing the azide group to a primary amino group —$NH_2$ and cleaving the hydroxyl masking groups $R_{10}$ to form said 3-aminonocardicinic acid.
9. A process according to claim 8 wherein $R_{10}$ is methyl.
* * * * *